(12) United States Patent
Lamrani

(10) Patent No.: US 10,478,104 B2
(45) Date of Patent: Nov. 19, 2019

(54) GLUCOSE SENSING CONTACT LENS

(71) Applicant: Menicon Co. Ltd., Nagoya (JP)

(72) Inventor: Mouad Lamrani, Geneva (CH)

(73) Assignee: MENICON CO., LTD., Nagoya (JP)

( * ) Notice: Subject to any disclaimer, the term of this patent is extended or adjusted under 35 U.S.C. 154(b) by 0 days.

(21) Appl. No.: 16/351,342

(22) Filed: Mar. 12, 2019

(65) Prior Publication Data

US 2019/0282140 A1  Sep. 19, 2019

Related U.S. Application Data

(60) Provisional application No. 62/642,176, filed on Mar. 13, 2018.

(51) Int. Cl.
| | | |
|---|---|---|
| *A61B 5/1455* | (2006.01) | |
| *A61B 5/145* | (2006.01) | |
| *G02C 7/04* | (2006.01) | |
| *A61B 5/00* | (2006.01) | |
| *G01N 33/66* | (2006.01) | |

(52) U.S. Cl.
CPC ........ *A61B 5/14532* (2013.01); *A61B 5/1455* (2013.01); *A61B 5/6821* (2013.01); *G01N 33/66* (2013.01); *G02C 7/04* (2013.01); *A61B 5/0075* (2013.01); *A61B 5/14507* (2013.01); *A61B 5/14546* (2013.01); *G01N 2800/042* (2013.01); *G01N 2800/50* (2013.01)

(58) Field of Classification Search
CPC . A61B 5/14532; A61B 5/1455; A61B 5/6821; A61B 5/14507; G02C 7/04
See application file for complete search history.

(56) References Cited

U.S. PATENT DOCUMENTS

| | | | | |
|---|---|---|---|---|
| 6,681,127 | B2* | 1/2004 | March | A61B 5/14532 600/319 |
| 8,446,341 | B2* | 5/2013 | Amirparviz | A61B 5/1455 250/221 |
| 8,870,370 | B1* | 10/2014 | Otis | G02C 7/04 351/159.03 |
| 2011/0117661 | A1 | 5/2011 | Daunert et al. | |
| 2012/0245444 | A1* | 9/2012 | Otis | A61B 5/1486 600/345 |
| 2018/0267331 | A1* | 9/2018 | Abbasi | G02C 7/049 |

FOREIGN PATENT DOCUMENTS

WO  2014209657 A1  12/2014

OTHER PUBLICATIONS

International Search Report and Written Opinion for International Application No. PCT/IB2019/000239, dated Jul. 9, 2019.

* cited by examiner

*Primary Examiner* — Eric F Winakur
(74) *Attorney, Agent, or Firm* — Dorsey & Whitney LLP

(57) ABSTRACT

A contact lens includes a glucose sensor which can determine when a detectable concentration of glucose is present in the optical fluids of the user. The glucose sensor can transition between a first state and a second state relative to the concentration of glucose within the optical fluid of the user. The glucose sensor can be bonded or otherwise attached or incorporated into the contact lens. While the contact lens is worn in the user's eye, either the user or another person can view the contact lens to quickly determine if an excessive amount of glucose is present in the user's system.

18 Claims, 11 Drawing Sheets

GLUCOSE SENSING CONTACT LENS

CROSS-REFERENCE TO RELATED APPLICATIONS

This application claims priority to U.S. Provisional Patent Application No. 62/642,176 filed on Mar. 13, 2018, the disclosure of which is incorporated herein, in its entirety, by this reference.

BACKGROUND

Diabetes is a condition that affects about 8.5% of adults in the world. It is a major cause of blindness, kidney failure, heart attacks, stroke, and lower limb amputation. Diabetes is a chronic disease that occurs when either the pancreas does not provide enough insulin, or when the body cannot effectively use the insulin it produces. Insulin is a hormone that regulates blood sugar. Raised blood sugar, or hyperglycemia, is a common effect of uncontrolled diabetes, and can lead to serious complications and damage to the body.

People with diabetes need to monitor their blood sugar multiple times a day. Typically, this is performed with a glucometer which measures glucose levels using a sample of the user's blood. Glucometers generally require a pin prick or other invasive method to obtain a blood sample from a user. The pin prick can be painful, discomforting, and disruptive to a person's routine. Some patients can even develop calluses on their fingers from continuous finger pricking. As a result, people with diabetes cannot, and often do not, check their blood glucose levels as often as recommended. Some new blood sugar testing systems perform continuous glucose monitoring through skin contact. Glucose measurements obtained from skin samples, however, are less accurate than the traditional glucometer. Consequently, a reliable, less invasive method of testing glucose levels in diabetics is needed.

SUMMARY

According to one aspect of the present disclosure, a contact lens can be provided. The contact lens can include a body having a rearward-facing surface and a forward-facing surface. The rearward-facing surface can form a substantially concave surface. The rearward-facing surface can be configured to engage the surface of a user's eye. The forward-facing surface can form a substantially convex surface. The contact lens can include a glucose sensor operably coupled to the body. The glucose sensor can have a first state and a second state, wherein the glucose sensor is configured to transition between the first state and the second state relative to a concentration of glucose within the user's optical fluid.

The glucose sensor can be a first color in the first state and a second color in the second state. The glucose sensor can exhibit a first opacity in the first state and a second opacity in the second state. The second opacity can be more transparent than the first opacity. The contact lens can further include at least one protrusion configured to align the contact lens within the user's eye by contacting an eyelid of the user. The glucose sensor can be operably coupled to the forward facing surface of the body of the contact lens.

In another aspect, a contact lens system can be provided. The contact lens system can include a contact lens and a wireless receiver. The contact lens can include a body having an eye-contacting surface configured to contact the surface of a user's eye. The contact lens can further include a glucose sensor operably coupled to the body and configured to collect data relative to the concentration of glucose within a user's optical fluid. The contact lens can also include a wireless transmitter configured to transmit the data collected by the glucose sensor. The contact lens can include a transmitter power supply configured to power the wireless transmitter. The wireless receiver can include a transceiver module, a user interface module, a control module, a memory module, a processor module, and a receiver power supply. The transceiver module can be operably coupled to an antenna. The antenna can receive data transmitted by the wireless transmitter. The user interface module can be configured to receive an input from a user and emit an alert. The control module can be configured to control operational aspects of the contact lens system. The memory module can be configured to receive and maintain computer-readable information. The processor module can be configured to execute the computer-readable information stored within the memory module to operate the wireless receiver. The receiver power supply can provide electrical power to the modules of the wireless receiver. The alert can be emitted when the data received by the wireless receiver exceeds an alert threshold.

The operational aspect can include adjusting the alert threshold. The alert threshold can be a concentration of glucose measured by the glucose sensor that exceeds a user defined concentration. The user interface module can include a speaker configured to emit an audio alert when the concentration of glucose measured by the glucose sensor exceeds the alert threshold. The user interface module can include a display configured to emit a visual alert when the concentration of glucose measured by the glucose sensor exceeds the alert threshold. The glucose sensor can further include a first state and a second state, wherein the glucose sensor is configured to transition between the first state and the second state relative to a concentration of glucose within the user's optical fluid. The first state can exhibit a first color and opacity and the second state can exhibit a second color and opacity. The second opacity can be more transparent than the first opacity.

In another embodiment, a contact lens system is provided. The contact lens system can include a contact lens and a wireless receiver. The contact lens can include a body, a glucose sensing area, an optical sensor, a wireless transmitter, and a transmitter power supply. The body can include an eye-contacting surface configured to contact the surface of a user's eye. The glucose sensing area can be operably coupled to the body. The glucose sensing area can have a first state and a second state, wherein the glucose sensing area transitions between the first state and second state as a concentration of glucose varies within a user's optical fluid. The optical sensor can be exposable to light. The optical sensor can be configured to collect data when exposed to light. The wireless transmitter can be configured to transmit the data collected by the optical sensor. The transmitter power supply can be configured to power the wireless transmitter. The wireless receiver can include a transceiver module, a user interface module, a control module, a memory module, processor module, and a receiver power supply. The transceiver module can be operably coupled to an antenna. The antenna can receive data transmitted by the wireless transmitter. The user interface module can be configured to receive input from a user and emit an alert. The control module can be configured to control operational aspects of the contact lens system. The memory module can be configured to receive and maintain computer-readable information. The processor module can be configured to execute the computer-readable information stored within the memory module to operate the wireless receiver. The receiver power supply can provide electrical power to the modules of the wireless receiver. The glucose sensing area can prevent light from reaching the optical sensor when in the first state and allow light to pass through the glucose sensing area to reach the optical sensor when in the second state.

The glucose sensing area can have a first opacity in the first state and a second opacity in the second state. The second opacity can be more transparent than the first opacity. The alert can be emitted anytime data is received by the wireless receiver. The optical sensor can be coupled to the eye-contacting surface of the body of the contact lens. The contact lens system can further include a second contact lens. The second contact lens can collect data that can be compared to the data collected by the first contact lens. The wireless receiver can generate an alert based on the comparison.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers designate similar, but not necessarily identical, elements.

DETAILED DESCRIPTION

The principles described in the current disclosure include incorporating a glucose sensor into a contact lens which can determine when a threshold amount of glucose is present in optical fluids (e.g., tears). The glucose sensor can be bonded or otherwise operably attached or incorporated into the contact lens. In some embodiments, the glucose sensor can transition between a first state and a second state, based on a concentration of glucose within the optical fluids. For example, the first state can appear to an observer as a first color, transparency, or opacity, and the second state can appear to an observer as a second color, transparency, or opacity. Thus, while the contact lens is worn within the user's eye, either the user or another person observing the user's eye can view the glucose sensor of the contact lens to quickly determine if the threshold amount of glucose is present in the user's optical fluids.

Figure 1:
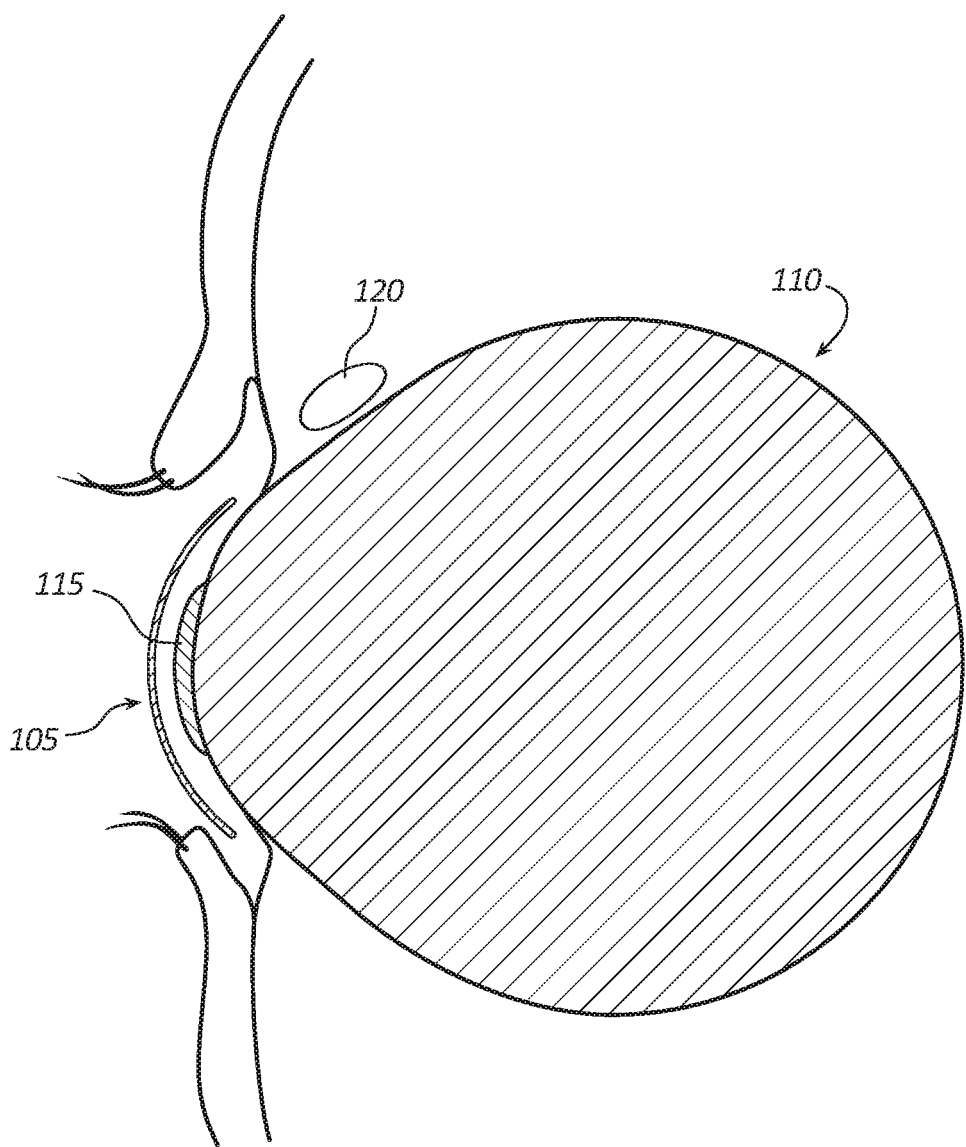
FIG. 1 illustrates a cross sectional view of an example of contact lens positioned on an eye in accordance with the present disclosure.

FIG. 1 depicts an example of a contact lens 105, according to the present disclosure. When a person closes an eyelid (e.g., by blinking or winking), the eyelid spreads optical fluid or tears onto the surface of the eye. This optical fluid is produced by the lacrimal gland 120 positioned above the eye 110. In some embodiments, a contact lens 105 of the present disclosure can sit atop the cornea 115 and contact optical fluid (e.g., tears) deposited by the eyelid. A glucose sensor (not shown), operably coupled to the contact lens 105, can measure the concentration of glucose within a user's tears. The glucose sensor (not shown) can dynamically transition between a first state and a second state relative to the concentration of glucose within the optical fluid.

The contact lens 105 can include a hard contact lens, a hydrogel lens, a silicone hydrogel lens, a hydrogel lens, an extended wear contact, a spherical contact, a toric contact, a multifocal contact, a monovision contact, a rigid gas permeable lens, a toric lens, and the like. In some embodiments, the contact lens 105 can incorporate a colored portion configured to change the appearance of a user's iris.

Any monomer material suitable for use in manufacturing the contact lens 105 can be used. In some embodiments, the monomer is HEMA/GMA. While this example has been described with reference to specific types of monomers that can be used to make the contact lens 105, any appropriate type of monomer or polymer can be used to construct the contact lens 105. Further, in other examples, silicon, polymers, other types of constituents, or combinations thereof can be used with the monomers, or in lieu of the monomers, for constructing the contact lens 105.

In some embodiments, additional materials can be used with the monomer to make the contact lens 105. Any additives for improving various characteristics of the contact lens 105 can be included therein. Examples of additives that can be used in conjunction with the monomer include, but are not limited to, thickeners, dyes, buffers, other types of additives, or combinations thereof. The amount of additive used in conjunction with the monomer can vary based on a variety of factors, including optical properties of the contact lens 105 and the desired characteristics imparted by the additives. Generally speaking, the additives are used in quantities that are sufficiently small that they do not significantly impact the mass of the resulting contact lens 105.

The contact lens 105 can be formed from any appropriate type of material. In some embodiments, the contact lens can be a hydrogel contact lens 105 or rigid gas permeable (RGP) contact lens 105. In some embodiments, the contact lens 105 can be a silicone hydrogel contact lens 105.

Other optical and structural properties of the contact lens 105 can be adjusted and/or fixed to produce a more comfortable and well performing contact lens 105. In some embodiments, the contact lens 105 includes a fixed base curve. In other words, the contact lens 105 can have the same volume of monomer and the same base curve across a wide range of powers. In some embodiments, the fixed base curve for the contact lens 105, across a range of powers, is selected from within a range of from 7.50 to 9.10.

Figure 2:
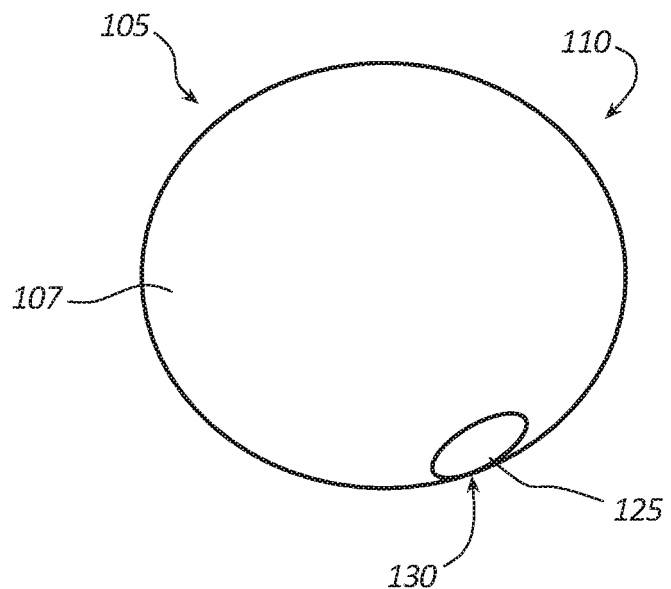
FIG. 2 illustrates an embodiment of a contact lens in accordance with the present disclosure.
Figure 3:
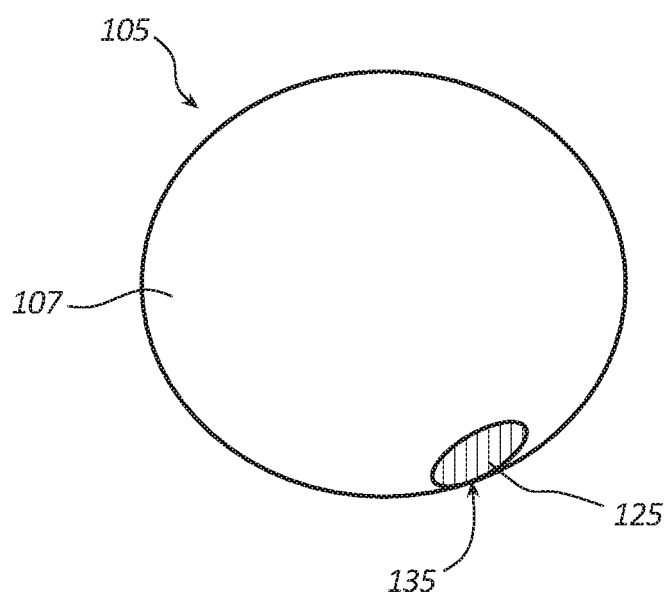
FIG. 3 illustrates an embodiment of a contact lens in accordance with the present disclosure.

FIGS. 2 and 3 depict examples of a contact lens 105 with glucose sensing capabilities. The contact lens 105 is shown with a glucose sensor 125 positioned on a periphery of the body 107 of the contact lens 105. The body 107 can include a rearward-facing surface and a forward-facing surface. The rearward-facing surface can have a substantially concave surface configured to contact the eye 110. The forward-facing surface can have a substantially convex surface. The glucose sensor 125 can be positioned at any location on the body 107 of the contact lens 105. In some embodiments, the glucose sensor 125 can be positioned on the forward-facing surface of the body 107 and away from a center of the body 107 of the contact lens 105 to prevent potential interference with a user's vision. In other embodiments, the glucose sensor 123 can be positioned on the forward-facing surface of the body 107 and near the center of the body 107 to blur a user's vision as an alert mechanism when glucose levels change the opacity of the glucose sensor. In some embodiments, an outside periphery of the body 107 can form a circle. In other embodiments, the outside periphery of the body 107 can form an oval. In one embodiment, a light source could be included in the contact lens adjacent to the sensor 123, allowing for the sensor to, either using the included light source or a natural or exterior light source, measure a change in turbidity, or loss of transparency. The turbidity measurement can evaluate intensity absorption and scattering of the light to determine changes in turbidity. When using natural light, the sensor can have a control (i.e. a measurement in a transparent area of the lens body 107), and can compare the change in turbidity relative to the control area.

A characteristic of the glucose sensor 125 can change in the presence of glucose. For example, the color or opacity of the glucose sensor 125 can vary, depending on the concentration of glucose within a user's optical fluid (e.g., tears). The glucose sensor 123 can be positioned on the rearward-facing surface of the body 107 of the contact lens 105 such that the glucose sensor 125 contacts fluid on the cornea of an eye (e.g., FIG. 1, cornea 115 of the eye 110) in some embodiments. In other embodiments, the glucose sensor 125 can be operably coupled to the forward-facing surface of the body 107 such that the user's eyelid deposits optical fluid onto the glucose sensor 125. A concentration of glucose can be present in the user's tears which can be indicative of an overall level of glucose present in the user's body and/or blood. If the amount of glucose present reaches a threshold, the user's health can be in danger. In some embodiments, the glucose sensor 125 can alter its appearance to visibly indicate when an excessive concentration of glucose is present.

For example, when a user places a new contact lens 105 over her cornea 115, the glucose sensor 125 can exhibit or assume a first state 130. An opacity of the first state 130 can be maintained or constant when a first concentration of glucose is present. For example the first concentration of glucose can include a range of glucose present in a person's system. The range can encompass what is considered a normal or healthy range for the general population, or for a specific user or population of users. In some embodiments, the range of users can include an amount that corresponds to a blood glucose level of about 80-180 milligrams of glucose per deciliter of blood. This range can include a normal, fasting glucose level, and can also incorporate a post-meal glucose level.

In some embodiments, the glucose sensor 125 can maintain the first state 130 when a healthy, acceptable range of glucose is present in a person's tears. In some embodiments, the first state 130 of the glucose sensor 125 can transition to a second state 135 when the glucose level has exceeded a threshold representing healthy glucose concentration. In further embodiments, the glucose sensor 125 can change to a second state 135 when the glucose level has been exceeded for a predetermined time period. For example, if the person's glucose level has surpassed a predetermined range for a predetermined duration of time, the state (e.g., appearance) of the glucose sensor 125 can change. Alternatively, if a person's glucose level has not surpassed a predetermined range for a predetermined period of time, the status of the glucose sensor 125 can remain unchanged. In other embodiments, the glucose sensor 125 can transition between a first state 130 and a second state 135 when a predetermined threshold of glucose is detected in the users system. For example, a single instance of a user's glucose concentration exceeding the predetermined threshold can cause the glucose sensor 125 to change appearance.

In one embodiment, the glucose sensor 125 can be a polymer which is prepared by an ultra-violet initiated free radical reaction. For example, acrylamidophenyl boronic acid, ethylene acrylate, and acrylic acid can be combined with a dimethyl sulfoxide solvent using methylenebisacrylamide as a cross-linker and 2,2-dimethoxy-2-phenylacetophenon as an initiator. The combination can be placed within a mold and then can be exposed to ultra-violet irradiation.

In another embodiment, the glucose sensor 125 can be a different polymer which is prepared by ultra-violet initiated free radical reaction. For example, acrylamidophenyl boronic acid, ethylene acrylate and dimethylacrylamide can be combined with a dimethyl sulfoxide solvent using methylenebisacrylamide as a cross-linker and 2,2-dimethoxy-2-phenylacetophenon as an initiator. The combination can be placed within a mold and can then be exposed to ultra-violet irradiation.

In some embodiments, the glucose sensor 125 can include a biosensor which can transition from the first state 130 to the second state 135 in response to a concentration of glucose present in a user's optical fluid. In some embodiments, the glucose sensor 125 can include an enzyme-free biosensor. The enzyme-free biosensor based glucose sensor 125 can be stable at room temperature and within the physiological conditions present in a user's eye. The biosensor can have a first appearance in the first state 130 and a second appearance in the second state 135.

For example, in some embodiments, the status of the glucose sensor 125 can exhibit at least two levels of opacity: a first opacity associated with the first state 130 for a first glucose level or range, and a second opacity for a second state 135 associated with a second glucose level or range. The first opacity can include an opaque or mostly opaque region located within the glucose sensor 125 on the contact lens 105. The opaqueness can have a color associate with it. For example, the first opacity can include a white opaque region on the contact lens 105. The size and shape of the opaque region can vary based on size of the contact lens and other factors. A second opacity can be mostly and/or completely transparent.

In some embodiments, the glucose sensor 125 can include a material which changes opacity in the presence of glucose. In some examples, the material can change opacity by a chemical reaction with glucose in a user's optical fluid. In some examples, the material can change opacity by a chemical reaction or series of chemical reactions with glucose and/or other chemicals in a user's optical fluid. In some embodiments, the glucose sensor 125 can be a boronic acid copolymer biomaterial. The glucose sensor 125 can react with glucose and change optical characteristics. In some embodiments, the glucose sensor 125 can include an enzyme-free material. It should be appreciated that the glucose sensor 125 can include any number of monomers, such that the glucose sensor 125 can be classified as a homopolymer, a copolymer, a terpolymer, or the like.

In some embodiments, the glucose sensor 125 can change color depending on the environment surrounding it. For example, in a healthy glucose range, the glucose sensor 125 can exhibit a first color. In a second, unhealthy, glucose range, the glucose sensor 125 can exhibit a second, different color. In some embodiments, the glucose sensor 125 can transition slowly to the second color to indicate a rise in glucose. For example, the first color can include red and the second color can include blue. As the user's glucose level rises, the glucose sensor 125 can change to varying shades of purple as the red color fades and the blue color emerges. In further embodiments, the opacity and color of the glucose sensor 125 can change. For example, the first state 130 can have a first opacity and a first color, for example white, associated with it. As the glucose level rises to an unhealthy level, the opacity of the first state 130 can begin to fade and, at the same time, the color of the glucose sensor 125 can change. The initial color and end color or opacity can include any combination of colors or opacity. In some cases, the first and second colors and opacity are different enough to be easily distinguishable with the naked eye. In other examples, opacity sensors and/or color sensors are used to determine when the glucose sensor 125 changes its state.

In some embodiments, the concentration of glucose present in a user's system can be easily characterized by viewing the glucose sensor 125. For example, a user can look in a mirror and be able to visibly see if the sensor is in the first state 130 or the second state 135, to quickly establish if the user has a healthy or unhealthy range of glucose in their system. Multiple observation methods can be utilized. For example, a third party can view the user's contact lens 105 and determine if the first or second state 130, 135 is present in the glucose sensor 125. A user can also use an image capturing device, such as a mobile device or a laptop, to photograph their eye, with the contact lens 105, and visibly distinguish between the first and second states 130, 135. The user can view the image herself, or she can transmit the image to a third party for observation and/or recordation purposes.

Figure 4:
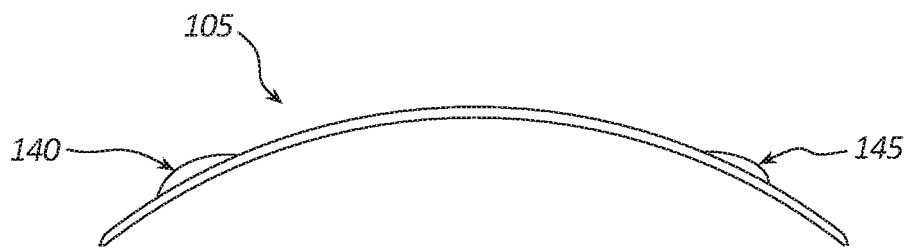
FIG. 4 illustrates a cross sectional view of an example of contact lens in accordance with the present disclosure.
Figure 5:
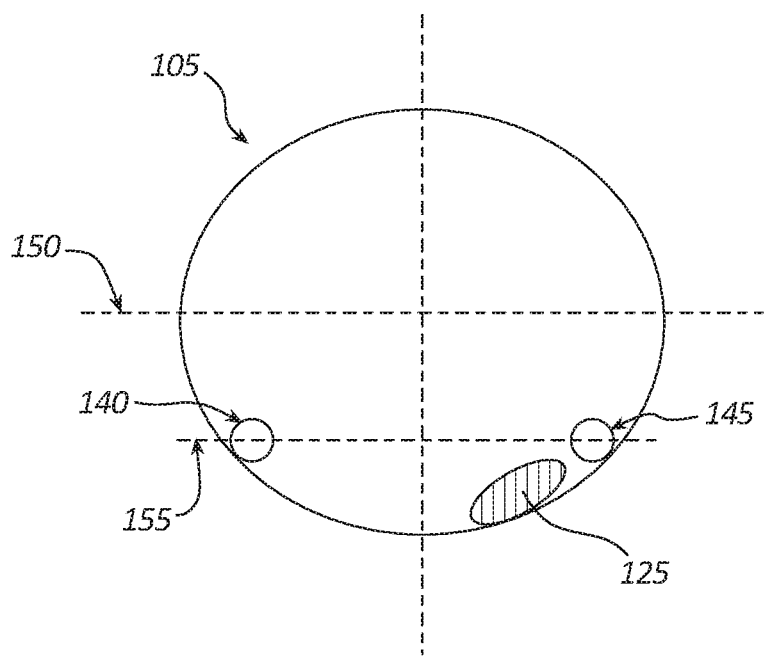
FIG. 5 illustrates an embodiment of a contact lens in accordance with the present disclosure.

In further embodiments, the contact lens 105 can align the glucose sensor 125 to be below an eyelid when worn in a user's eye. The contact lens 105 can incorporate one or more features to align the contact lens 105 such that the glucose sensor is visible and can be observed by the user or a third party. For example, FIGS. 4 and 5 display a contact lens 105 with one or more protrusions 140, 145. The protrusions 140, 145 can be biasing features configured to align the contact lens 105 in the eye in a desired and consistent orientation.

For example, a first protrusion 140 can be larger than a second protrusions 145. In some embodiments, the protrusions 140, 145 can extend from and protrude proud of the contact lens 105 by about 0.1 mm to about 3 mm, from about 0.25 mm to about 3 mm, from about 0.5 mm to about 3 mm, or from about 1 mm to about 3 mm. In some examples, one or more protrusions 140, 145 can extend more than about 3 mm from the contact lens 105. In some examples, one or more protrusions 140, 145 can extend less than about 0.1 mm from the contact lens. The protrusions 140, 145 can be multiple shapes and sizes. The protrusions 140, 145 can either be substantially symmetric or can be asymmetric.

When the contact lens is in use, the eyelid will interact with the contact lens 105. As the eyelid closes, the eyelid can contact one of the protrusions 140, 145 first. Depending upon the orientation of the contact lens 105 in the eye, the eyelid can contact either the first protrusions 140 or second protrusion 145. As the eyelid continues to move downward, the eyelid will contact a protrusion, for example the first protrusion 140. The first protrusion 140 will move downward with the eyelid and, eventually, the eyelid will contact the second protrusion 145. After the eyelid contacts the first protrusion 140, the contact lens 105 will rotate until the eyelid engages the second protrusion 145. When both protrusions 140, 145 engage the eyelid, the eyelid can overcome the resistance of the protrusions 140, 145 and slip over the protrusion 140, 145, thereby orienting the contact lens 105 in a desired orientation relative to the user's eye.

The protrusions 140, 145 can be located substantially centric to or below a centerline 150 of the contact lens 105. This can enable the protrusions 140, 145 to align the contact lens 105 within the eye such that the glucose sensor 125 is visible and is not hidden under a user's eyelid. For example, the glucose sensor 125 can be located substantially below either the centerline 150 of the contact lens 105 or a centerline 155 between the protrusions 140, 145. In some embodiments, at least one of the protrusions 140, 145 can include the glucose sensor. In other words, the glucose sensor can form a protrusion on the surface of the contact lens 105, in some embodiments.

Figure 6:
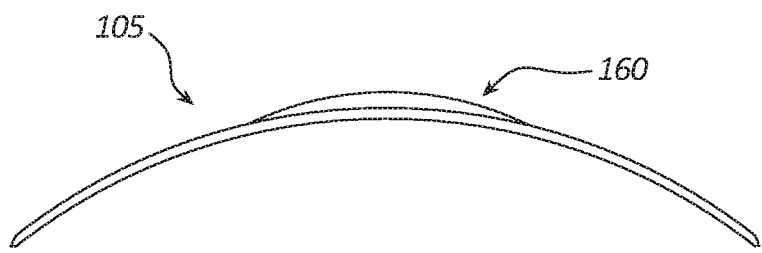
FIG. 6 illustrates a cross sectional view of an example of contact lens in accordance with the present disclosure.
Figure 7:
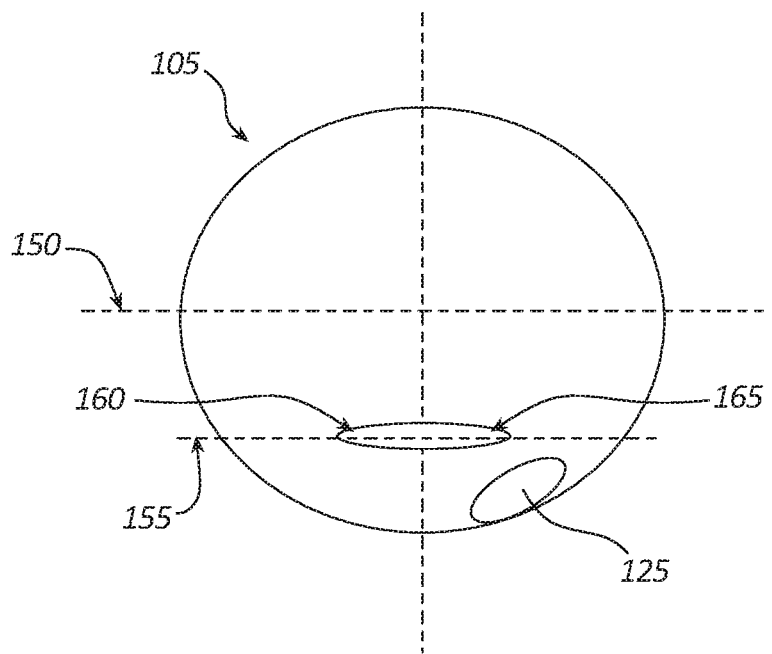
FIG. 7 illustrates an embodiment of a contact lens in accordance with the present disclosure.

FIGS. 6 and 7 depict an alternative embodiment of a protrusion 160. The protrusion 160 can be a single raised member on the contact lens 105. The protrusion 160 can be located below the centerline 150 of the contact lens 105. The protrusion 160 can have a substantive width such that the eyelid can contact an upper surface 165 of the protrusion 160, and the eyelid can orient the contact lens 105 into a desired rotational position within the eye. The desired orientation can locate the glucose sensor 125 below the eyelid such that the user or a third party can easily view the glucose sensor 125.

Figure 8:
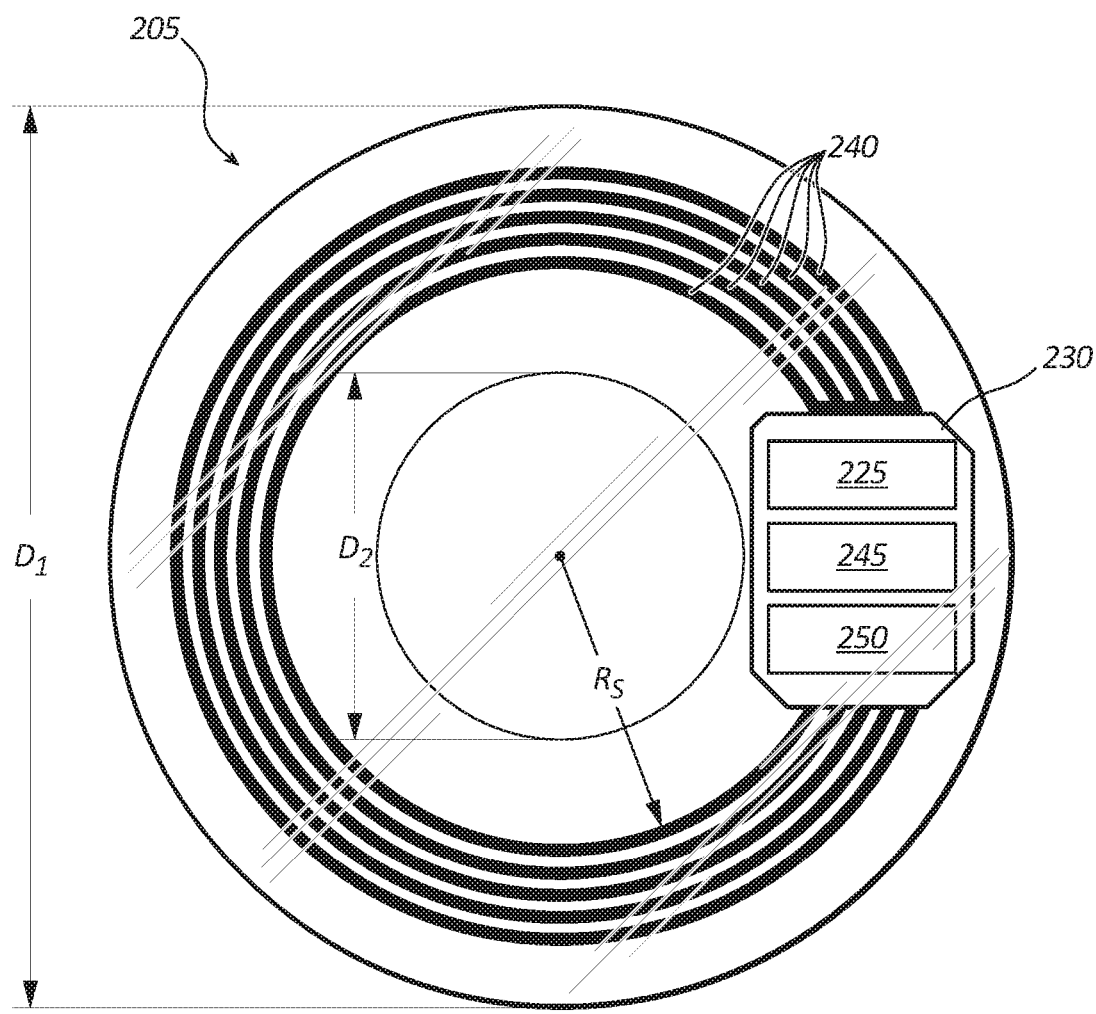
FIG. 8 illustrates an embodiment of a contact lens in accordance with the present disclosure.

FIG. 8 depicts an example schematic of a contact lens 205 for glucose sensing, according to the present disclosure. The contact lens 205 can include a printed circuit board (PCB) 230 operably coupled with an antenna 240. The PCB 230 can include or be operably coupled with any number of electrical components to detect and transmit glucose concentrations on a surface of the contact lens 205. In one embodiment, the PCB 230 includes a glucose sensor 225, a transmitter power supply 245, and a wireless transmitter 250. The glucose sensor 225 can be configured to detect or otherwise measure a concentration of glucose on the surface of the contact lens 205. The glucose sensor 225 can be operably connected to the wireless transmitter 250. The wireless transmitter 250 is operably coupled to the antenna 240 and the transmitter power supply 245 to facilitate transmitting signals relative to glucose detection. In one embodiment, the antenna 240 can include multiple loops that span a periphery of the contact lens 205, as depicted in FIG. 8.

The position at which the PCB 230 and the antenna 240 are coupled to the contact lens 205 can vary. For example, the PCB 230 and the antenna 240 can be operably coupled to, yet be encapsulated by, the forward-facing surface of the contact lens 205, in one embodiment. In another embodiment, the PCB 230 and the antenna 240 can be operably coupled to, and be encapsulated by, the rearward-facing surface of the contact lens 205. Moreover, the PCB 230 and the antenna 240 can also be coupled in varying positions relative to the line of sight of the contact lens wearer. For example, the antenna 240 can be positioned at a radius $R_S$ from the center of the contact lens 205 as to avoid obstructing the wearer's vision. Similarly, the PCB 230 can be operably coupled outside of a dimension $D_2$ as to not obstruct the wearer's vision. Alternatively, a component of the contact lens 205 can be positioned near the center of the contact lens 205 as to obscure the vision of the wearer. For example, the glucose sensor 225 can be positioned at the center of the contact lens 205 and configured to change color or opacity to alert the wearer that a threshold glucose concentration has been exceeded.

The PCB 230 and the antenna 240 can be an RFID sensor-tag that has been incorporated onto or into the contact lens 205, in some embodiments. The RFID sensor-tag can include a sensor or multiple sensors that are sensitive to light and an RFID sensor. The RFID sensor-tag can also include a microcontroller unit configured to control operational aspects of the RFID sensor-tag (e.g., transmitting and receiving signals, power delivery and consumption, etc.). The RFID sensor-tag can also include an antenna (e.g., a multiple loop antenna). The RFID sensor-tag can be printed on a flexible polyimide substrate such as Kapton®. The RFID sensor-tag can be wirelessly powered using, for example, an RFID repeater device positioned near the contact lens 205. Moreover, the RFID repeater device can also be utilized to receive data or other signals transmitted by the RFID sensor-tag.

Figure 9:
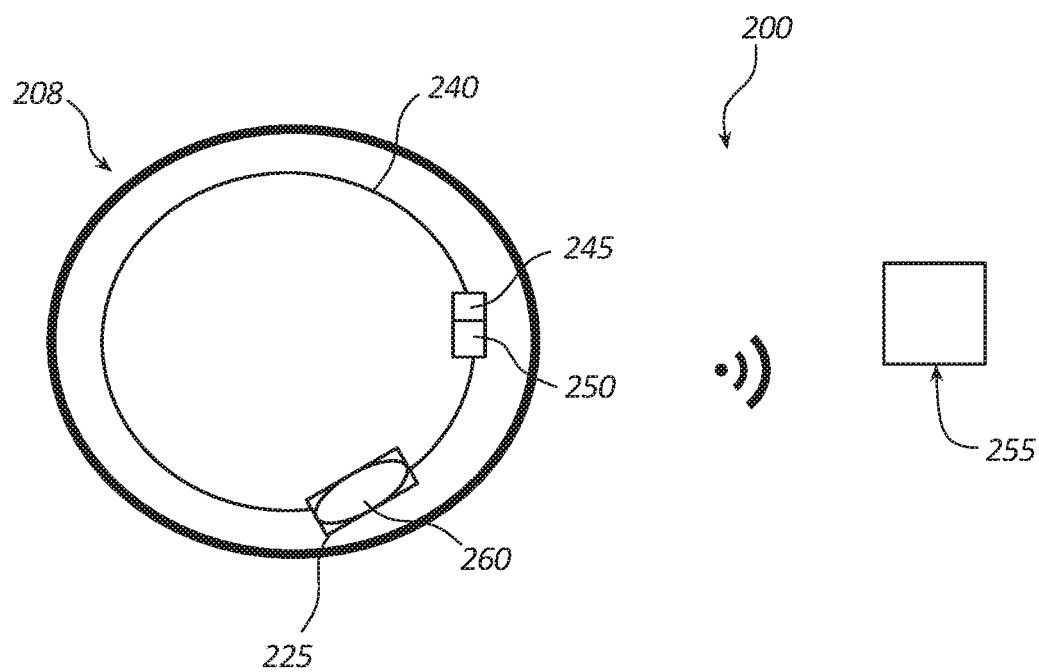
FIG. 9 illustrates an embodiment of a contact lens system in accordance with the present disclosure.

FIG. 9 depicts an example of a contact lens system 200 for glucose sensing according to the present disclosure. The contact lens system 200 can include a contact lens 208 and a wireless receiver 255. An example of contact lens 208 can include the contact lenses described with reference to FIGS. 1-8. In some embodiments, the contact lens 208 can include a glucose sensor 225, an antenna 240, a transmitter power supply 245, a wireless transmitter 250, and a glucose sensing area 260. The glucose sensor 225 can be identical to or similar to the glucose sensors described with reference to FIGS. 2-8. In some embodiments, a contact lens 208 can communicate wirelessly with the wireless receiver 255 by transmitting data to the wireless receiver 255 via the antenna 240.

Figure 10:
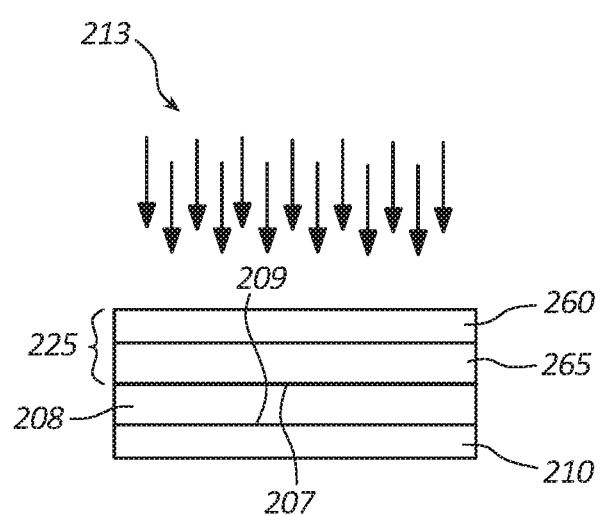
FIG. 10 illustrates a cross sectional view of an example of glucose sensor operably coupled to a contact lens in accordance with the present disclosure.

FIG. 10 depicts a cross sectional view of a glucose sensor 225 operably coupled to a contact lens 208, according to one embodiment of the present disclosure. The glucose sensor 225 can include a glucose sensing area 260 and an optical sensor 265. The glucose sensor 225 can be positioned on the outer portion of the contact lens 208 facing away from the eye 210 (e.g., operably coupled to the forward-facing surface 207 of the contact lens 208). The optical sensor 265 can be operably coupled to the glucose sensing area 260. For example, the optical sensor 265 can be positioned between the glucose sensing area 260 and the contact lens 208. The glucose sensing area 260 can have similar attributes as the glucose sensor 125 described with reference to FIGS. 2-7. For example, the glucose sensing area 260 can transition between a first state and a second state. The first state and second state can be similar to the first state 130 and second state 135, as described with reference to FIGS. 2-3. The first state can have a first opacity, transparency, color, or a combination thereof, and the second state can have a second opacity, transparency, color, or combination thereof relative to the concentration of glucose within the user's optical fluid. The glucose sensing area 260 can dynamically transition between the first and second state as the concentration of glucose within the user's tears or optical fluid vary.

The optical sensor 265 can initially be shielded or obscured from light 213 by the glucose sensing area 260 in a first state. As the glucose sensing area 260 transitions from the first state to the second state, the optical sensor 265 can gradually become partially or fully exposed to light 213. As the optical sensor 265 becomes exposed to light 213, the optical sensor 265 can begin to take measurements or otherwise collect data.

In the first state, the glucose sensing area 260 can be opaque to prevent light 213 from passing through the glucose sensor 225, thereby preventing the optical sensor 265 from receiving light 213. When the glucose concentration in a user's tears reaches a predetermined threshold (e.g., an unhealthy concentration of glucose), the glucose sensing area 260 can transition to the second state. The glucose sensing area 260 can be more transparent in the second state to allow light 213 to pass through the glucose sensor 225 and be received by the optical sensor 265.

In one embodiment, the optical sensor 265 can include a thin-film solar cell. The optical sensor 265 can include one or more thin layers of thin film of photovoltaic material on a substrate. The substrate can include a plastic. The optical sensor 265 can vary from a few nanometers thick, up to tens of micrometers thick. As the solar cell is exposed to light 213, the solar cell operating as the optical sensor 265 can begin to charge the transmitter power supply 245. As the transmitter power supply 245 is charged, the transmitter power supply 245 can power the antenna 240 and begin to transmit one or more signals, communications, or data to the wireless receiver 255. The transmission can include predetermined communications regarding a concentration of glucose in a user's optical fluid. In some embodiments, the transmission can be a simple communication relaying that the optical sensor 265 has been exposed to light 213. Thus, alerting the wearer that a threshold concentration of glucose has been reached or exceeded.

In some embodiments, the optical sensor 265 can additionally and/or alternatively include a photometer sensor or an ambient light sensor. The optical sensor 265 can measure light intensity or the optical intensity. The optical sensor 265 can measure illuminance, irradiance, light absorption, scattering of light, reflection of light, fluorescence, phosphorescence, luminescence, turbidity, and the like. The optical sensor 265 can detect light using at least one of a photoresistor, a photodiode, photomultipliers, or the like. In some embodiments, the optical sensor 265 can measure an amount of light after it has passed through a filter or monochromator. The use of a filter or monochromator can enable the optical sensor 265 to determine light intensity at defined wavelengths, or to analyze a spectral distribution of the light.

In other embodiments, the optical sensor 265 can measure individual photons rather than incoming flux. Flux can include spectral flux or spectral power of the light that reaches the optical sensor 265. In some embodiments, the optical sensor 265 can include a reflectance photometer which can measure the reflectance of a surface as a function of wavelength.

In some embodiments, the optical sensor 265 can alternatively or additionally measure the absorption of light of a given wavelength. For example, the optical sensor 265 can measure the concentration of a colored substance in a solution. The optical sensor 265 can include an absorption photometer to measure ultraviolet and visible ranges of specific light wavelengths.

The optical sensor 265, as a photometer, can collect and feed data to the wireless transmitter 250. The wireless transmitter 250 can transmit data or other signals to the wireless receiver 255 through the antenna 240 powered by the transmitter power supply 245. For example, as the optical sensor 265 is exposed to light 213, the optical sensor 265 can begin measuring various optical attributes, as discussed. When the optical measurements reach a predetermined threshold, the optical sensor 265 can feed data to the wireless transmitter 250. The wireless transmitter 205 can then transmit the data to the wireless receiver 255. In one embodiment, as the glucose sensing area 260 transitions from a first state of opacity to a second state of opacity, the change in opacity can allow higher concentrations of light 213 to permeate the glucose sensing area 260, and thereby expose the optical sensor 265 to higher concentrations of light 213. Thus, the opacity of the glucose sensing area 260 can act as a temporary barrier which only allows light to pass when there is an unhealthy concentration of glucose within the user's optical fluid.

In some embodiments, the optical sensor 265 can act as a capacitor. For example, the optical sensor 265 can store a charge which can be released when the optical sensor 265 is exposed to light 213, for example, when the glucose sensing area 260 transitions from the first state to the second state. As the optical sensor 265, as a capacitor, is exposed to light 213, the capacitor can build up a charge and subsequently release the charge to power the transmitter power supply 245. Once the transmitter power supply 245 is powered, the antenna 240 can transmit data or other signals to the wireless receiver 255.

The transmitter power supply 245 can include a battery operably coupled to the contact lens 205. The battery can be rechargeable. The transmitter power supply 245 can initially have a stored charge or the transmitter power supply 245 can be charged by the optical sensor 265. The transmitter power supply 245 can include graphene. In some embodiments, the transmitter power supply 245 can be printed to a surface of the contact lens. The transmitter power supply 245 can be a graphene printed battery. In some embodiments, the transmitter power supply 245 can be fully printable, and can include a planar architecture. In some embodiments, the transmitter power supply 245 can be flexible and have a long shelf-life. The transmitter power supply 245 can function in a moist environment. In some embodiments, the transmitter power supply 245 can have approximately one microampere per square millimeter capacity per unit area. The transmitter power supply 245 can include approximately twenty-five microampere per cubic centimeter capacity per unit volume.

In some embodiments, the transmitter power supply 245 can be capable of wirelessly charging. For example, the transmitter power supply 245 can receive power wirelessly from an electronic device (not shown) positioned near the transmitting power supply 245. In one embodiment, a repeater device having an RFID reader can be positioned near the contact lens 205 and can be configured to wirelessly transmit the power sufficient to operate the transmitter power supply 245 and/or the glucose sensor 225.

Figure 11:
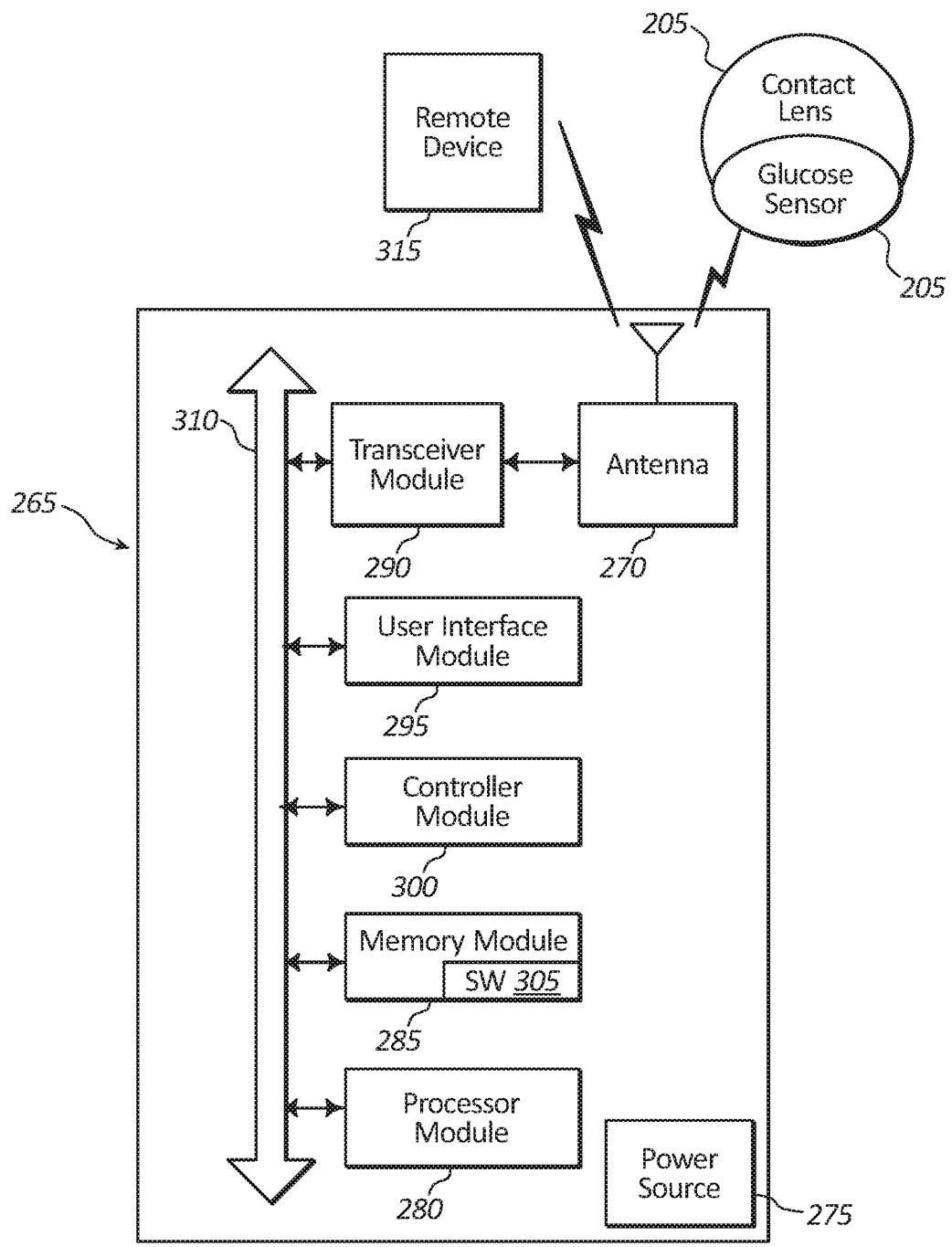
FIG. 11 illustrates a block diagram of an example wireless receiver in accordance with the present disclosure.

An embodiment of the wireless receiver 255 is shown in FIG. 11. The wireless receiver 255 can include a receiver power supply 275. The wireless receiver 255 can also include a processor module 280, and memory module 285 (including software/firmware code (SW) 305), a control module 300, a user interface module 295, a transceiver module 290, and one or more antennas 270, each of which can communicate—directly or indirectly—with one another (e.g., via one or more buses 310). The transceiver module 290 can communicate bi-directionally via the antenna 270 with the contact lens 205. For example, the transceiver module 290 can receive data or other communication media from one or more contact lenses 205. In some embodiments, the transceiver module 290 can communicate bi-directionally with one or more contact lenses 205. In some embodiments, the transceiver module 290 can further communicate bi-directionally with a remote device 315. The remote device 315 can include one or more of a mobile device, a laptop, a repeater device, or another device. The transceiver module 290 can modulate packets to send to the antenna 270 for transmission, and to demodulate packets received from the antenna 270. While the wireless receiver 255 can include a single antenna 270, the wireless receiver 255 can also have multiple antennas capable of concurrently transmitting or receiving multiple wireless transmissions.

In some embodiments, the wireless receiver 255 can be a repeater device positioned near the contact lens 205 (e.g., integrated into a pair of eyeglass frames). The repeater device can include an RFID reader, a microcontroller, and/or a transmitting antenna. Operation of the wireless receiver 255 can be controlled via a cloud server in wireless communication with a microcontroller within the wireless receiver 255. Moreover, transmission data received at the wireless receiver 255 from the contact lens 205 can be recorded on the cloud server.

The receiver power supply 275 can be operably coupled to each module within the wireless receiver 255 to provide electrical power. In some embodiments, the receiver power supply 275 can include a battery configured to accommodate mobile operation of the wireless receiver 255. In other embodiments, the receiver power supply can include a bridge circuit configured to convert a continuous supply of alternating current (i.e., AC) to direct current (i.e., DC) to power the hardware components of the wireless receiver 255. For example, the receiver power supply 275 can plug directly into an electrical outlet.

In some embodiments, the wireless receiver 255 can connect to a remote device via a wired transmission. In some embodiments, one element of the wireless receiver 255 (e.g., antenna 270, transceiver module 290, etc.) can provide a connection using wireless techniques, including digital cellular telephone connection, Cellular Digital Packet Data (CDPD) connection, digital satellite data connection, and/or another connection. The signals associated with wireless receiver 255 can include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 270 and/or transceiver module 290 can include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, the antenna 270 can include a plurality of antennae which can receive signals or information specific and/or exclusive to individual antennae.

The user interface module 295 can receive input from an operator (e.g., a physician) or a user of the wireless receiver 255. For example, the user or operator of the wireless receiver 255 can input periodic time intervals in which glucose data is collected, transmitted, or received. The user interface module 295 can also allow a user or operator to input or modify a minimum threshold of glucose concentration that must be reached before the user interface module 295 emits an alert. Additionally, a user or operator can input a minimum number of instances in which a glucose concentration threshold is exceeded before an alert is triggered. For example, an alert can be triggered when the threshold is met or exceeded five times within a two hour period. Similarly, a user or operator can input a time duration in which the glucose concentration is required to exceed the threshold before an alert is triggered. For example, an alert can be triggered when the measured glucose concentration exceeds a minimum threshold for at least thirty minutes.

In some embodiments, the user interface module 295 can include an audio device, such as an external speaker system, a visual display, and/or an input device. A speaker can provide an audible output when a glucose concentration has reached or exceeded a predetermined threshold. For example, once the glucose concentration reaches an unhealthy level, as detected by a glucose sensor (e.g., glucose sensor 225), the wireless receiver 255 can receive a communication and can emit an audible alert to the user. In some embodiments, a visual display such as a screen or a light can additionally or alternatively alert the user of a detected unhealthy glucose concentration.

One or more buses 310 can allow data communication between one or more modules of the wireless receiver 255 (e.g., processor module 280, memory module 285, control module 300, user interface module 295, etc.).

The memory module 285 can include random access memory (RAM), read only memory (ROM), flash RAM, and/or other types of memory. The memory module 285 can store computer-readable information, computer-executable software/firmware code 305 including instructions that, when executed, cause the processor module 280 to perform various functions described in this disclosure (e.g., receiving an alert concerning glucose concentration, communicating an alert to the user, etc.). The processor module 280 can process data received by the antenna 270 and prepare data for transmission (e.g., encode, multiplex, and packetize data to be transmitted to the contact lens 205). The processor module 280 can compare data to the threshold concentration and actuate the user interface module 295 to emit an alert or an alarm. The processor module 280 can also cause processed data to be stored within the memory module 285 as a time log for review by the user or a physician. The processor module 280 can make calculations based on the glucose concentration data (e.g., averages, medians, trends, etc.). The processor module 280 can process commands input into the user interface module 295 by a user.

The control module 300 can be configured to control operational aspects of the contact lens system. In some embodiments, the control module 300 can control the intervals in which glucose concentration data is collected and transmitted by the contact lens 205. The control module 300 can also control the interval in which transmissions from the contact lens 205 are received by the wireless receiver 255. In other embodiments, the control module 300 can control which types of data the contact lens is collecting (e.g., glucose concentration, illuminance, irradiance, light absorption, scattering of light, reflection of light, fluorescence, phosphorescence, luminescence, etc.). The control module 300 can also actuate or otherwise implement user or operator input received through the user interface module 295.

Figure 12:
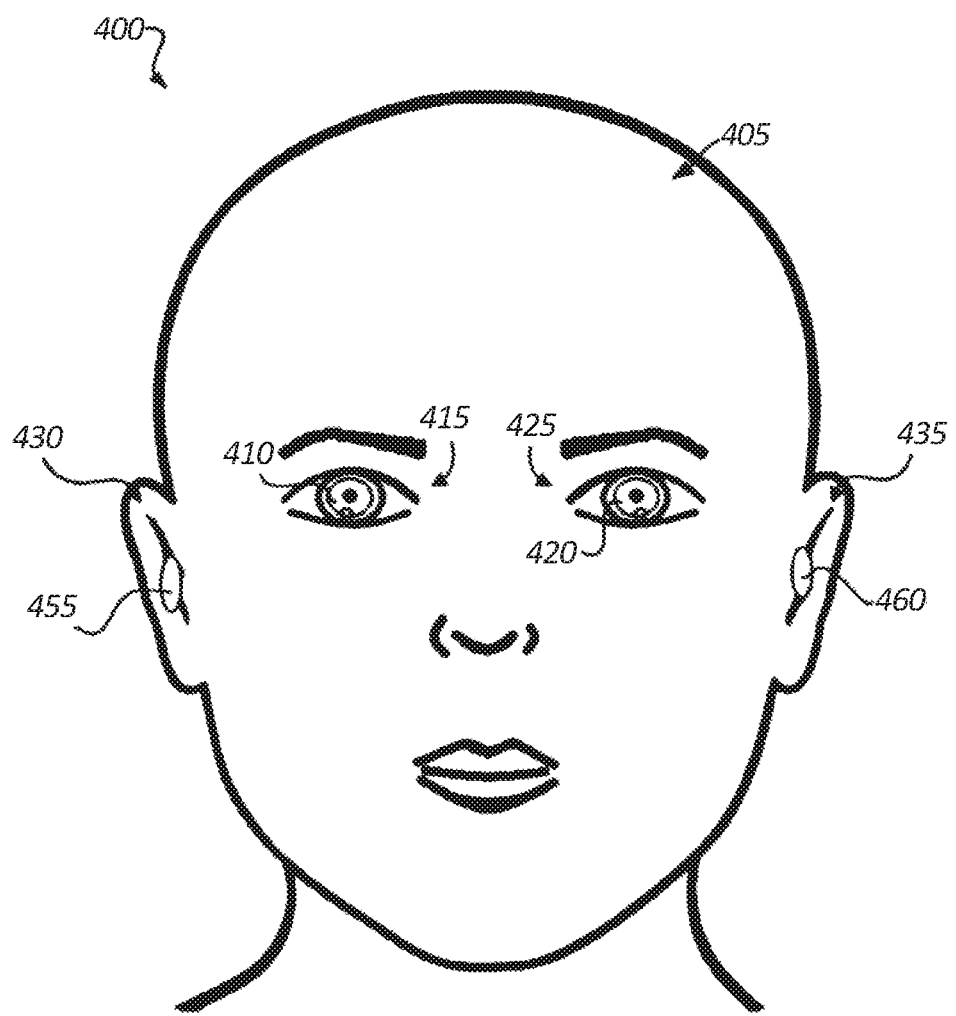
FIG. 12 illustrates an embodiment of a contact lens system in accordance with the present disclosure.

FIG. 12 is a schematic of a contact lens system 400 being worn by a user 405. The user 405 can have a first contact lens 410 in a first eye 415 and a second contact lens 420 in a second eye 425. A wireless receiver 455 can be in a first ear 430. In some embodiments, a second wireless receiver 460 can be in a second ear 435. The first contact lens 410 can be a contact lens as discussed with reference to FIGS. 8-10. The second contact lens 420 can additionally be a contact lens as discussed with reference to FIGS. 8-10.

For example, each contact lens 410, 420 can detect a glucose concentration present in the tear fluid of the user 405. The wireless receivers 455, 460 can be worn in a respective ear closest to the coupling contact lens 410, 420. Having the wireless receiver 455, 460 mountable in or proximate to the user's ear 430, 435 provides a consistent short distance between the contact lens 410, 420 and the wireless receiver 455, 460. The consistent distance provides predictability in the strength of signal needed from the contact lens 410, 420 to the wireless receiver 455, 460. Having a wearable wireless receiver 455, 460 also provides that the receiver will remain within the predetermined distance. It should be appreciated that the wireless receivers 455, 460 can be positioned proximate to the contact lenses 410, 420 (e.g., operably coupled to a pair of eyeglass frames, a hat, etc.). The wireless receiver 455, 460 can alert the user to an unhealthy glucose concentration and can transmit a signal to a device associated with the user to communicate a glucose concentration.

In some embodiments, the contact lenses 410, 420 can each detect glucose concentration and thereby provide a dual detection system for detecting unhealthy glucose concentrations within the user. In alternative embodiments, one of the contact lenses, for example, the second contact lens 420, can include a control contact lens. The control contact lens can include an antenna and a power supply similar to the contact lens referenced in FIGS. 1-10. In some embodiments, however, the control contact lens can include an optical sensor without the glucose sensing area. By having a contact lens with only the optical sensor, the optical sensor can transmit optical data to the wireless receiver to alert the user that their contact lens is functioning properly or improperly. In alternative embodiments, one or more of the contact lenses 410, 420 can include the glucose sensor as well as an additional optical sensor. The additional optical sensor can continuously communicate a first message to the wireless receiver 455, 460 ensuring the components of the contact lens 410 is working properly. Furthermore, the use of a control contact lens can allow the overall system to identify a differential (e.g., by making a comparison) with respect to the light or energy being measured or collected by the optical sensor. This can reduce false positive alerting based on changes in ambient light or other changes relative to the user's environment.

Figure 13:
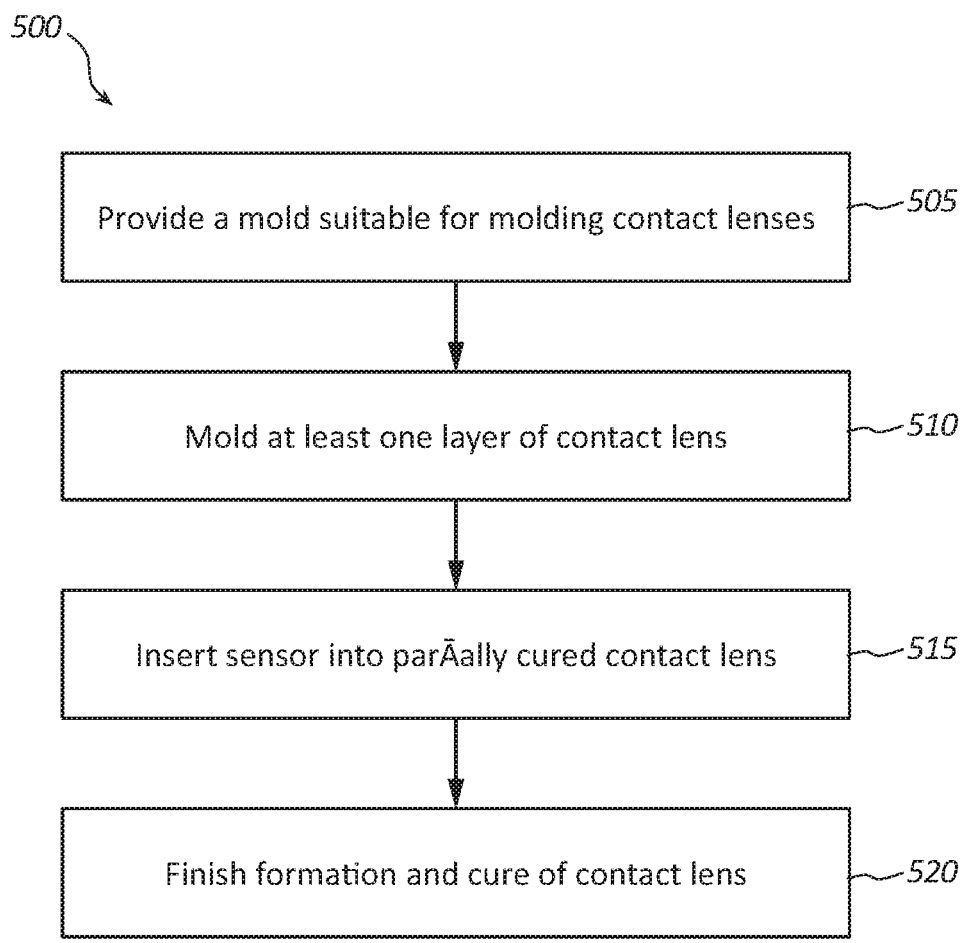
FIG. 13 illustrates a block diagram of an example of a method of using a glucose sensor in accordance with the present disclosure.

FIG. 13 illustrates an example of a method 500 of making a contact lens. In this example, the method 500 includes providing a mold suitable for molding contact lenses 505, molding various layers of the contact lens 510, inserting the sensor structure into the contact lens 515, and finish the formation and cure of the contact lens 520.

At block 505, a master mold is generated. The master mold has the profile of the ultimate contact lens being formed. The mold can include a low surface material such as PTFE. This can prevent adhesion to the mold. The mold can alternatively include other materials and then be coated with PTFE or other suitable low surface energy material. In some cases, the mold can include a metallic or a ceramic material, or composites thereof. More particularly, the mold that is generated can be a female mold for cast molding, or, in the present example, the mold can be a mold configured for use in spin casting a contact lens. According to this exemplary embodiment, the surface of the spin casting mold includes the shape and features to be formed on the front surface of the ultimately formed contact lens.

At block 510, multiple layers of the contact lens can be formed. In the example where the lens is a spin casted lens, monomer can be deposited into the mold, and the mold can be rotated to distribute the monomer, while the monomer is partially cured, or cured to a gel state.

At block 515, the sensor is inserted into the body of the contact lens. According to one exemplary embodiment, the sensor can be pre-formed and inserted into the mold prior to the insertion and partial curing of the monomer, as described at block 510.

In an alternative embodiment, the sensor can be formed in a separate mold and inserted into the partially cured contact lens described in block 510. According to this exemplary embodiment, the sensor is formed in a mold mimicking the ultimate contact lens mold. The mimicking mold is coated with different layers of the sensor structure. For example the mold can be coated via printing, dipping, or spin coating the layers onto the mold. Upon completion, the sensor structure is formed atop the mold. In one example, the sensor structure is removed from the mold. For example, the sensor structure can be lifted from the mold using a separate tool that attaches to the sensor structure. The tool can include a tacky surface. For example, the tool can include a Sylgard® silicone gel or any other material suitable for use in removing structure from a mold. Once removed, the sensor structure can be pressed into the partially cured contact lens. For example, the sensor structure can be a separate entity and can be pressed against the partially cured contact lens for few seconds to establish a bond to form between the contact lens and the sensor structure. The bond can include polydimethylsiloxane (PDMS) and hydrogel or silicone hydrogel. If the sensor structure includes a first layer with PDMS, the PDMS layer can be tailored with alginate to enhance a bond between the sensor structure with PDMS and the hydrogel or silicone hydrogel.

Once the bond is formed, the formation and cure of the contact lens can be completed 520. According to one embodiment, additional monomer can be deposited in the mold encapsulating the sensor. For example the sensor structure can be coated with hydrogel, silicone hydrogel, or other suitable materials, or combinations thereof. The coating can surround and encapsulate the sensor structure onto the contact lens.

Figure 14:
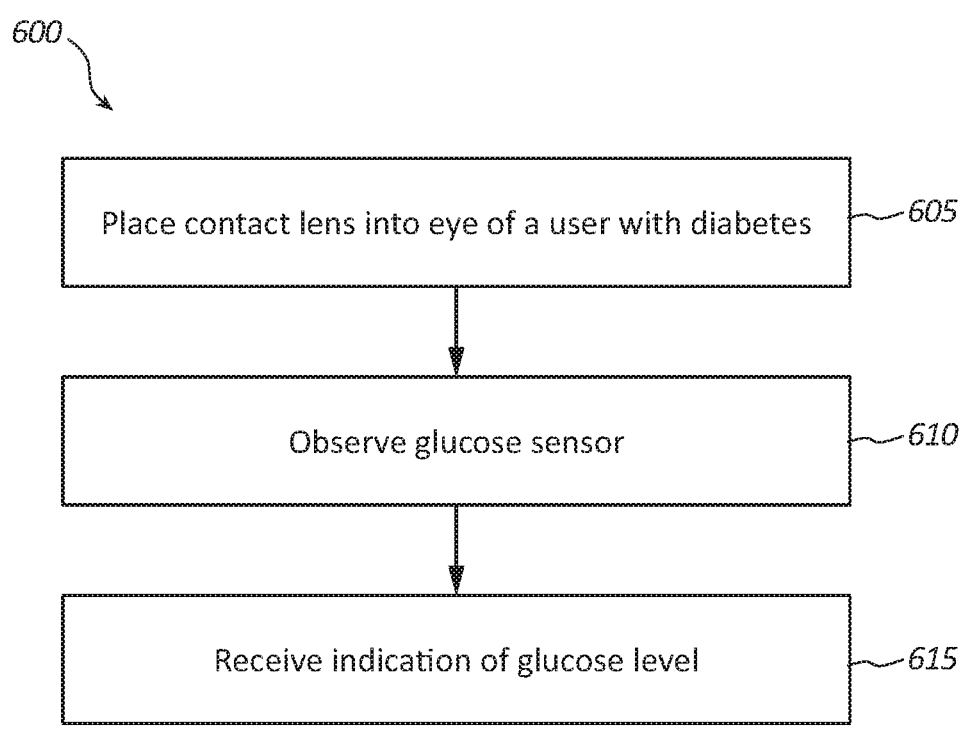
FIG. 14 illustrates a block diagram of an example of a method of using a glucose sensor in accordance with the present disclosure.

FIG. 14 illustrates an example of a method 600 of using a contact lens. In this example, the method 600 includes placing a contact lens onto an eye of a user with diabetes 605, observing the glucose sensor 610, and receiving an indication of a glucose level of the user 615.

At block 605, the contact lens is placed in the eye of a user. The use of the sensor can be most effective if the user has a confirmed case of diabetes or signs indicative of someone with diabetes. At block 610, the glucose sensor is observed. The user can observe their own glucose sensor via a mirror, or picture (e.g. a selfie or other self-photograph, reflection, or other method of viewing ones-self). At block 615, the method 600 can include receiving an indication of a glucose level. In some embodiments, the indication can include a change in the glucose sensor from the first state to the second state. For example, the glucose sensor can have a nonvisible first state which can transition to a visible second state. The transition between the first state and second state can indicate to the user or a third party that the glucose concentration has reached an unhealthy level. In other embodiments, a third party can view the glucose sensor and notify the user. In another embodiment, the glucose sensor can be a sensor and can automatically detect a level of glucose in the user's system. The glucose sensor can communicate to a remote device. The remote device can communicate an alert to user relating to the user's glucose concentration. In some embodiments, a lack of communication from the glucose sensor can indicate an acceptable glucose level in the user's system. Once the sensor structure begins to communicate with remote sensor, the user can be alerted to an unhealthy glucose concentration level in their system. In some embodiments, the user can also request the status of glucose concentration from the remote device.

Example

Figure 15:
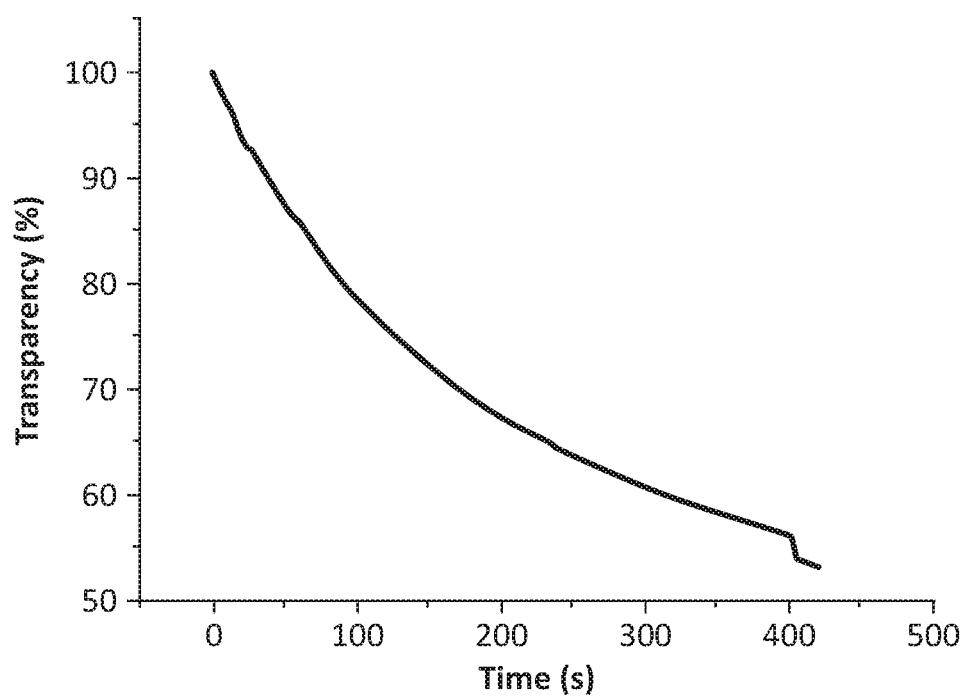
FIG. 15 illustrates a graphical representation of the transparency of a glucose sensor exposed to a concentration of glucose over a period of time, according to one embodiment.

In order to further clarify the specifics of the present disclosure, one embodiment of the present disclosure will be described in detail in reference to FIG. 15. A polymer glucose sensor was prepared utilizing ultra-violet initiated free radical reaction. The polymer glucose sensor was created by combining acrylamidophenyl boronic acid, ethylene acrylate, and acrylic acid in a dimethyl sulfoxide solvent. Methylenebisacrylamidewas used as a cross-linker, and 2,2-dimethoxy-2-phenylacetophenon was used as an initiator. The combination was then placed into a mold and exposed to ultra-violet irradiation.

The polymer glucose sensor was submerged in a phosphate buffer solution (pH=7.4) containing 1M of D-glucose. The polymer glucose sensor was then positioned between a light source and a digital ambient light sensor (e.g., OPT3001 from Texas Instruments). The transparency of the polymer glucose sensor was then measured over a time interval of 420 seconds to create the graph depicted in FIG. 15. As shown in FIG. 15, the transparency of the polymer glucose sensor decreased by nearly 50% as the polymer glucose sensor remained submerged in the solution. This demonstrated differential in transparency of the polymer glucose sensor can be utilized to visually or digitally communicate a concentration of glucose within the tear fluid of a contact lens wearer.

In one embodiment disclosed herein, a contact lens includes a body and a glucose sensor operably coupled to the body. The glucose sensor can have a first state and a second state. According to this example, the glucose sensor is configured to transition between the first state and the second state in response to a concentration of glucose within the user's optical fluid.

In one embodiment, the glucose sensor is a first color in the first state and a second color in the second state. In on embodiment, the glucose sensor has a first opacity in the first state and a second opacity in the second state. In one embodiment, the second opacity is more transparent than the first opacity. In an alternative embodiment, the second opacity is less transparent than the first opacity In one embodiment, the contact lens can include at least one protrusion configured to align the contact lens within the user's eye.

In one embodiment, the glucose sensor is operably coupled to a forward-facing surface of the body of the contact lens.

In another embodiment disclosed herein, a contact lens system includes a contact lens and a wireless receiver. The contact lens can include a body having a proximal surface and a distal surface, a glucose sensor operably coupled to the body, the glucose sensor being configured to collect data relative to a concentration of glucose within a user's optical fluids, a transmitter communicatively coupled to the glucose sensor, and a transmitter power supply coupled to the wireless transmitter. The wireless receiver can include an antenna configured to be communicatively coupled to the transmitter, a transceiver module operably coupled to the antenna, a control module communicatively coupled to the contact lens system, a memory module coupled to the system, the memory module configured to receive and maintain computer-readable information, a processor module communicatively coupled to the memory module, the processor being configured to execute the computer-readable information stored within the memory module to operate the wireless receiver, a receiver power supply, and a user interface module configured to receive input from a user and emit an alert, wherein the alert is emitted when the wireless receiver receives data from the contact lens that exceeds an alert threshold.

In one example of the contact lens system, the control module is configured to facilitate modification of the alert threshold, the alert threshold being a concentration of glucose measured by the glucose sensor that exceeds a user defined concentration.

In one example of the contact lens system, the user interface module further includes a speaker and/or a display.

In one example of the contact lens system, the glucose sensor is configured to exhibit a first state and a second state, the glucose sensor being configured to transition between the first state and the second state in response to a concentration of glucose within the user's optical fluid, the first state having a first color and the second state having a second color.

In one example of the contact lens system, the glucose sensor has a first opacity in the first state and a second opacity in the second state. In one example, the second opacity is more transparent than the first opacity.

According to yet another exemplary embodiment, a contact lens system includes a contact lens. The contact lens includes a body having an eye-contacting surface configured to contact the surface of a user's eye, a glucose sensing area operably encapsulated within the body, the glucose sensing area having a first state and a second state, wherein the glucose sensing area transitions between the first state and the second state as a concentration of glucose varies within a user's optical fluids, an optical sensor disposed between the eye contacting surface and the glucose sensing area, a transmitter communicatively coupled to the optical sensor, and a power supply coupled to the wireless transmitter.

In one example of the contact lens system, the glucose sensing area has a first opacity in the first state and a second opacity in the second state. In one example, the second opacity is more transparent than the first opacity.

In one example of the contact lens system, the system further includes a wireless receiver. The wireless receiver can include a transceiver module operably coupled to an antenna, the transceiver module being configured to receive the data transmitted by the wireless transmitter, a user interface module configured to receive input from the user and emit an alert, a control module configured to control operational aspects of the contact lens system, a memory module configured to receive and maintain computer-readable information, a processor module configured to execute the computer-readable information stored within the memory module to operate the wireless receiver, and a receiver power supply. In exemplary embodiment, the glucose sensing area prevents light from reaching the optical sensor while in the first state and allows light to pass through the glucose sensing area to reach the optical sensor while in the second state, and the alert is emitted anytime data is received by the wireless receiver.

In one example of the contact lens system, the optical sensor is coupled to the eye-contacting surface of the body of the contact lens.

In one example of the contact lens system, the system further includes a second contact lens, wherein data collected by the second contact lens is compared to the data collected by the first contact lens. According to this embodiment, the wireless receiver is configured to emit an alert if an anomaly is detected by the comparison.

It should be noted that any of the features in the various examples and embodiments provided herein can be interchangeable and/or replaceable with any other example or embodiment. As such, the discussion of any component or element with respect to a particular example or embodiment is meant as illustrative only. In addition, it should be noted that the methods described above describe possible implementations, and that the operations and the steps can be rearranged or otherwise modified and that other implementations are possible. Furthermore, aspects from two or more of the methods can be combined.

All relative and directional references (including: upper, lower, upward, downward, left, right, leftward, rightward, top, bottom, side, above, below, front, middle, back, vertical, horizontal, and so forth) are given by way of example to aid the reader's understanding of the particular examples described herein. They should not be read to be requirements or limitations, particularly as to the position, orientation, or use unless specifically set forth in the claims. Connection references (e.g., attached, coupled, connected, secured, joined, and the like) are to be construed broadly and can include intermediate elements between a connection of elements and relative movement between elements. As such, connection references do not necessarily infer that two elements are directly connected and in fixed relation to each other, unless specifically set forth in the claims. Moreover, in some embodiments, the teachings of the present disclosure can be utilized on contact lenses having additional ancillary purposes (e.g., pressure sensing, etc.).

The description herein is provided to enable a person skilled in the art to make or use the disclosure. Various modifications to the disclosure will be readily apparent to those skilled in the art, and the generic principles defined herein can be applied to other variations without departing from the scope of the disclosure. Thus, the disclosure is not limited to the examples described herein, but is to be accorded the broadest scope consistent with the principles and novel features disclosed herein.

I claim:

1. A contact lens, comprising:
   a body; and
   a glucose sensor operably coupled to the body, the glucose sensor having a glucose sensing area and an optical sensor, the glucose sensing area being configured to transition between a first state and a second state in response to a variance in glucose concentration;
   wherein the glucose sensing area prevents the passage of light through the glucose sensing area to the optical sensor in the first state and permits the passage of light through the glucose sensing area to the optical sensor in the second state, the optical sensor being configured to generate an output in response to detecting light.

2. The contact lens of claim 1, wherein the glucose sensing area is a first color in the first state and a second color in the second state.

3. The contact lens of claim 1, wherein the glucose sensing area has a first opacity or turbidity in the first state and a second opacity or turbidity in the second state.

4. The contact lens of claim 3, wherein the second opacity is more transparent than the first opacity.

5. The contact lens of claim 1, further comprising at least one protrusion configured to align the contact lens within a user's eye.

6. The contact lens of claim 1, wherein the glucose sensor is operably coupled to a forward-facing surface of the body of the contact lens.

7. The contact lens of claim 1, further comprising a light source disposed adjacent to the glucose sensor to enable a measurement of turbidity.

8. A contact lens, comprising:
a body having a concave surface and a convex surface;
a glucose sensor operably coupled to the body, the glucose sensor comprising:
an optical sensor positioned adjacent to the convex surface of the body; and
a glucose sensing area configured to transition between a first state and a second state in response to a variance in glucose concentration, the glucose sensing area overlaying the optical sensor;
wherein the glucose sensing area prevents the passage of light through the glucose sensing area to the optical sensor in the first state and permits the passage of light through the glucose sensing area to the optical sensor in the second state, the optical sensor being configured to generate an output in response to detecting light.

9. The contact lens of claim 8, wherein the glucose sensing area has a first opacity in the first state and a second opacity in the second state.

10. The contact lens of claim 9, wherein the second opacity is more transparent than the first opacity.

11. The contact lens of claim 8, wherein the optical sensor is operably coupled to a transmitter, the transmitter being configured to transmit a signal in response to the output.

12. The contact lens of claim 8, wherein the glucose sensing area is a first color in the first state and a second color in the second state.

13. A contact lens system, comprising:
a contact lens, comprising:
a body having an eye-contacting surface configured to contact the surface of a user's eye;
a glucose sensing area operably encapsulated within the body, the glucose sensing area having a first state and a second state, wherein the glucose sensing area transitions between the first state and the second state as a concentration of glucose varies;
an optical sensor disposed between the eye contacting surface and the glucose sensing area;
a transmitter communicatively coupled to the optical sensor; and
a power supply coupled to the wireless transmitter; and
a wireless receiver, comprising:
a transceiver module operably coupled to an antenna, the transceiver module being configured to receive the data transmitted by the wireless transmitter;
a user interface module configured to receive input from the user;
a control module configured to control operational aspects of the contact lens system;
a memory module configured to receive and maintain computer-readable information;
a processor module configured to execute the computer-readable information stored within the memory module to operate the wireless receiver; and
a receiver power supply;
wherein the glucose sensing area prevents light from reaching the optical sensor while in the first state and allows light to pass through the glucose sensing area to expose the optical sensor to the light while in the second state.

14. The contact lens system of claim 13, wherein the glucose sensing area has a first opacity in the first state and a second opacity in the second state.

15. The contact lens of claim 14, wherein the second opacity is more transparent than the first opacity.

16. The contact lens system of claim 13, wherein the optical sensor is coupled to the eye-contacting surface of the body of the contact lens.

17. The contact lens system of claim 13, further comprising a second contact lens, wherein data collected by the second contact lens is compared to the data collected by the first contact lens.

18. The contact lens system of claim 17, wherein the wireless receiver is configured to emit an alert if an anomaly is detected by the comparison.

* * * * *